(12) United States Patent
Zervos

(10) Patent No.: US 7,288,546 B1
(45) Date of Patent: Oct. 30, 2007

(54) METHOD AND COMPOUND FOR INHIBITION OF CELL DEATH

(75) Inventor: Antonis S. Zervos, Orlando, FL (US)

(73) Assignee: University of Central Florida, Orlando, FL (US)

( * ) Notice: Subject to any disclaimer, the term of this patent is extended or adjusted under 35 U.S.C. 154(b) by 530 days.

(21) Appl. No.: 10/369,311

(22) Filed: Feb. 20, 2003

(51) Int. Cl.
- *A01N 43/54* (2006.01)
- *A61K 31/515* (2006.01)
- *C07D 239/02* (2006.01)

(52) U.S. Cl. ................................. 514/270; 544/314

(58) Field of Classification Search ............ 514/270; 544/314
See application file for complete search history.

(56) References Cited

U.S. PATENT DOCUMENTS

| | | | |
|---|---|---|---|
| 6,004,794 A | 12/1999 | Karran | 435/226 |
| 6,245,773 B1 | 6/2001 | Wong et al. | 514/272 |
| 2002/0010186 A1 | 1/2002 | Wong et al. | 514/258 |
| 2003/0229108 A1* | 12/2003 | De Belin et al. | 514/269 |

OTHER PUBLICATIONS

Cilenti, L.; Lee, Y.; Hess, S.; Srinivasula, S.; Park, K.; Junqueira, D; Davis, H.; Bonventre, J.; Alnemri, E.; Zervos, A. "Characterization of a Novel and Specific Inhibitor for the Pro-apoptotic Protease Omi/HtrA2", Mar. 2003, The Journal of Biological Chemistry, vol. 278 (13), pp. 11489-11494.*

Nicholson, Donald W., From Bench to Clinic with Apoptosis-Based Therapeutic Agents, *Nature*, vol. 407, Oct. 12, 2000, pp. 810-816.

Faccio, Lucia, et al., Characterization of a Novel Human Serine Protease That has Extensive Homology to Bacterial Heat Shock Endoprotease HtrA and is Regulated by Kidney Ischemia, *The Journal of Biological Chemistry*, vol. 275, No. 4, Jan. 28, 2000, pp. 2581-2588.

Hedge, Ramesh, et al., Identification of OMI/HtrA2 as a Mitochondrial Apoptotic Serine Protease that Disrupts Inhibitor of Apoptosis Protein-Caspase Interaction, *The Journal of Biological Chemistry*, vol. 277, No. 1, Jan. 4, 2002, pp. 432-438.

* cited by examiner

*Primary Examiner*—Sreeni Padmanabhan
*Assistant Examiner*—Kendra D Carter
(74) *Attorney, Agent, or Firm*—Thomas J. Engellenner; George A. Xixis; Nutter McClennen & Fish, LLP

(57) ABSTRACT

This invention relates to a chemical compound that inhibits the apoptotic activity of the protease Omi/HtrA2 and homologous proteins. This protease Omi/HtrA2 is present in all mammalian cells so that inhibition of apoptosis in this fashion results enhanced cellular health and therapeutic effects.

4 Claims, No Drawings

METHOD AND COMPOUND FOR INHIBITION OF CELL DEATH

This invention relates to a protease and more particular to a chemical compound that inhibits the apoptotic activity of the protease Omi/HtrA2, and method for using such compound for therapeutic use.

BACKGROUND AND PRIOR ART

Many of today's medical diseases can be attributed directly or indirectly to problems with apoptosis—a programmed cell-suicide mechanism. Disorders in which defective regulation of apoptosis contributes to disease pathogenesis or progression can involve either cell accumulation, in which cell eradication or cell turnover is impaired, or cell loss, in which the cell-suicide program is inappropriately triggered. Identification of the genes and gene products that are responsible for apoptosis, together with emerging information about the mechanisms of action and structures of apoptotic regulatory and effector proteins, has laid a foundation for the discovery of drugs, some of which are now undergoing evaluation in human clinical trials.

Typically, one thinks of cell death as being a pathological phenomenon, but in fact, each second nearly one million cells commit suicide in the adult human body. In an average day, we produce, and in parallel eradicate, ~60×10$^9$ cells which represents a mass of cells equivalent to an entire body weight on an annual basis. This massive flux of cell birth and death occurs in the self-renewing tissues of the body (skin, gut, bone marrow and sex organs), providing mechanisms for rapidly regulating cell numbers by controlling the rates of both input and elimination. Physiological cell death has important roles in a wide variety of normal processes, ranging from fetal development to ageing, and including: immune system education, for which potentially autoreactive cells are eliminated; defense against viruses, for which altruistic cell suicide can deny viral replication within a host; tissue homeostasis, for which cell production is offset by commensurate cell eradication, thereby ensuring appropriate total cell numbers in vivo; and many aspects of reproductive biology.

Programmed cell death is vital to the existence of virtually all organisms, As a result, knowledge about programmed cell-suicide mechanisms can have broad ramifications for devising strategies for protecting crops, interfering with insect and parasite life cycles, tissue engineering and ex vivo cell production, and the development of human therapeutics. Physiological or programmed cell death generally occurs by apoptosis and defects in the physiological pathways for apoptosis have a role in many diseases. A reasonable estimate is that either too little or too much cell death contributes to half of the main medical illnesses for which adequate therapy or prevention is lacking. Consequently, great interest has emerged in devising therapeutic strategies for modulating the key molecules that make life-or-death decisions in cells.

Apoptosis is generally caused by proteases known as "caspases". Caspases constitute a family of intracellular cysteine proteases that cleave substrates at aspartic acid (Asp) residues. Produced initially as inactive zygomens, caspases are triggered into action generally as a result of their proteolytic processing at conserved Asp residues. Because caspases both cleave their substrates at Asp residues and are also activated by proteolytic processing at Asp residues, these proteases can collaborate in proteolytic cascades, in which caspases activate themselves and each other. Within these cascades, caspases can be positioned as downstream effectors of apoptosis.

U.S. Pat. No. 6,004,794 discloses isolated nucleic acids encoding a human serine protease PSPI, protein obtainable from the nucleic acids, recombinant host cells transformed with the nucleic acids, oligonucleotides and primer pairs specific for PSP1 polymorphisms and use of the protein and nucleic acid sequences. This patent thus discloses the Omi/HtrA2 which has been identified as a mitochondrial apoptotic serine protease that also disrupts the inhibition of apoptosis protein-caspase interaction.

Since the Omi/HtrA2 is present in all mammalian cells and by its activity of disrupting the inhibition of the "apoptosis protein-caspase interaction" decreases the cell lifetime, it would be most important to discover an inhibitor of the adverse activity of Omi/HtrA2 and homologous proteins.

SUMMARY OF THE INVENTION

The first objective of the present invention is to discover one or more inhibitors of Omi/HtrA2.

The second objective of the invention is to identify an inhibitor of Omi/HtrA2 which reduces the inhibition of the cellular apoptosis protein-caspase interaction.

The third objective of the invention is to discover an inhibitor of L56 protein.

The fourth objective of the invention is to discover an inhibitor of bacterial HtrA.

The fifth objective of the invention is to provide a method for screening for compounds which inhibit apoptosis.

The sixth objective of the invention is to provide a method for screening for compounds which inhibit Omi/HtrA2.

The preferred embodiments of invention identifies a chemical inhibitor of Omi/HtrA2 whose structure is

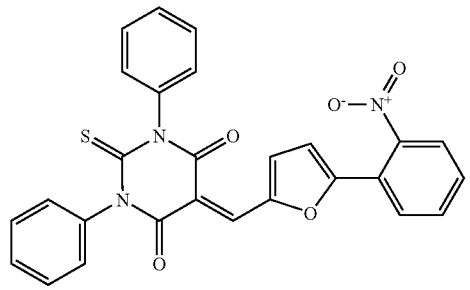

and its use in the inhibition of excessive mammalian apoptosis.

Further objects and advantages of this invention will be apparent from the following detailed description of the presently preferred embodiments.

DESCRIPTION OF THE PREFERRED EMBODIMENT

Before explaining the disclosed embodiment of the present invention in detail, it is to be understood that the invention is not limited in its application to the details of the particular arrangement shown since the invention is capable of other embodiments. Also, the terminology used herein is for the purpose of description and not of limitation.

It would be useful to discuss the meanings of some words used herein and their applications before discussing the novel compound of the invention and its inhibition activity:

apoptosis—an active process of programmed cell death characterized by distinct morphological changes in the cell caspases—a family of intracellular cysteine proteases that generally are responsible for apoptosis;

inhibitor of apoptosis protein (IAP)—contains at least one copy of Baculovirus IAP of a repeat (BIR) domain and suppresses apoptosis when overexpressed and is known to bind and inhibit caspases;

zymogen—the inactive proform of an enzyme which is typically activated by proteolysis The invention as noted from the prior art is concerned basically with the discovery that the activity of Omi/HtrA2 and homologous proteins are inhibited by a compound of the structure

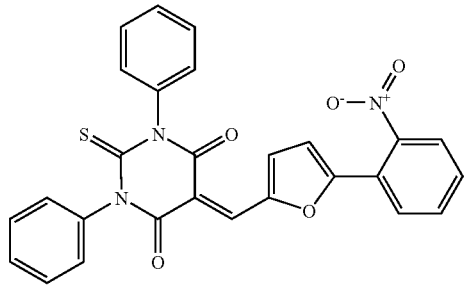

This structure, whose chemical name is 5-{5-(2-nitro-phenyl)-furan-2-ylmethylene}-1,3-diphenyl-2-thioxo-dihydro-pyrimidine-4,6-dione will hereinafter be referred to as UCF 101.

Moreover, Omi/HtrA2 also has homology with other cellular proteins, such as L56, another mammalian protein, and bacterial HtrA at the carboxyl terminus of the polypeptides. Thus inhibition of these proteins with UCF 101 is also indicated. While Om/HtrA2 is sequestered primarily in the mitochondria, L56 is not and therefore may be even more susceptible to inhibition. L56 has been shown to be differentially expressed in human osteoarthritic cartilage. Further, bacteria which lack HtrA are less virulent and thus inhibition by UCF 101 effectively results in its use as an antibiotic.

By targeting the caspase directly by inhibiting the Omi/Htr/A2 activity which reduces the inhibition of the cellular apoptosis protein-caspase interaction, or by virtue of its serine-protease activity the following applications of the invention are prospectively useful when excessive apoptosis in a human is present:

ischemia-reperfusion injury (stroke, myocardial infarction). In addition to apoptotic cell death, necrosis is also present;

heart failure—(loss of myocardiocytes);

neuro-degeneration—(Alzheimer's disease, Parkinson's disease, Hntington's disease and amytrophic lateral sclerosis);

inflammation;

osteoarthritis;

human immunodeficiency virus—(loss of T lymphocytes);

bacterial infection—apoptosis-inducing virulence proteins are secreted into the cytosol of host cell. (Examples are *Shigella* spp, *Salmonella* spp, *Yersinia* spp and *Chlamydia* spp.);

allograft rejection and graft versus host disease;

type 1 diabetes; and, trauma (spinal-cord injury, brain injury).

EXAMPLE 1

Omi shows proteolytic activity in the following assay that uses β-casein as a generic substrate. 528 compounds were screened for inhibition of this assay, and the sole compound which resulted in inhibited activity was UCF 101:

Preparation of FITC-Labeled Unphosphorylated Casein (FITC-Casein). FITC (Fluorescein Isothiocyanate), 37.5 mg, was dissolved in 2.5 ml DMSO. 1.6 ml of this FITC solution was added with stirring to 800 ml Borate buffer (50 mM Sodium Borate, pH 9.3, 40 mM NaCl) to make a final solution of 0.03 mg FITC/ml. 3 ml of casein (2 mg/ml) was placed in "A Slide-A-Lyzer" Dialysis Cassettes (Pierce, Ill.) and then placed in freshly prepared labeling solution (Borate buffer and FITC), covered with aluminum foil and left at 4° C. for 2 days with continuous stirring. After labeling, the "A Slide-A-Lyzer" cassette was placed in dialysis buffer (50 mM Tris-HCl, pH7.5 and 50 mM NaCl) for four days at 40 C with stirring to remove uncoupled FITC. After this time the casein-FITC conjugate was removed and stored at −20° C. in the dark.

Protease assay using MBP-Omi$_{134-458}$ and FITC-casein. Opaque microtiter plates were used to minimize background and assays were always performed in duplicate. In a typical assay, approximately 10 μg (50 μl) FITC-casein solution was placed in each well of a microtiter plate well using Multidrop 384 multiple dispenser (Labsystems), and incubated in the Wallac 1420 Victor$^2$ Multilabel Counter at 37° C. for 15 minutes. After this time 50 μl (2 μg) of MBP-Omi$_{134-458}$ in 100 μl of assay buffer (20 mM Sodium Phosphate, pH7.5, 200 mM NaCl, 5% Glycerol) were added. After one minute delay, the fluorescence change was read every 5 minutes during 30 minutes at 535 nm. The relative rate for each reaction was calculated using the fluorescence change in the initial 20 minutes after subtracting the blank values (no MBP-Omi$_{134-458}$).

Synthesis and purification of MBP-Omi$_{134-458}$.

pMAL-c2 prokaryotic expression vector (New England Biolabs) was used to express f MBP-Omi$_{134-458}$. DNA primers were designed to PCR amplify the DNA sequence corresponding to amino acids 134 to 458. The PCR fragment was cloned into pMAL-c2 to express the Omi$_{134-458}$ as a fusion with MBP. The recombinant protease was purified on a Maltose-binding affinity column following a standard protocol (NEB). The concentration of fusion protein was determined using the Bradford assay. Integrity and purity of the protein was assessed by SDS-PAGE.

Combinatorial library screening. Six plates of Pharma Library Collection (Nanosyn, Inc, Calif.) representing a total of 528 compounds were screened for inhibition of the proteolytic activity of MBP-Omi$_{134-458}$. 58 μl of DMSO was added to each well containing 30 nmole of a compound (2 μl) to make 500 μM final solution. 2 μl of each of the compounds was added per well in a microtiter plate followed by 50 μl of a FITC-casein solution (10 ug); after 15 min. preincubation at 370 C, 50 μl of MBP-Omi$_{134-458}$. (2 ug) protease was added. After one minute delay, fluorescence change was monitored every 5 minutes for 30 minutes at 535 nm.

EXAMPLE 2 study using ucf-101 inhibitor to block apoptosis.

Mouse embryo fibroblasts caspase-9-/- were transfected with pEGFP-N1 as control and M-Omi-GFP, in presence or absence of ucf-101 at increasing concentration (5 to 25 μM). The percentage of apoptotic cells were determined using propidium iodide and 4',6'-diamidino-2-phenylindole stains. Normal and apoptotic GFP-expressing cells were counted using fluorescence microscopy. Transfected cells treated with inhibitor ucf-101 showed decreased apoptosis HeLa cells were transfected with mature Omi (aa134-458), Omi-AVPS-GFP and mature Omi where the first Alanine (A) was mutated to a Glycine. Omi-GVPS-GFP transfected cells were treated with increasing concentration of ucf-101. Overexpression of mature Omi-GVPS-GFP can induce apoptosis only through its ability to function as an active protease (caspase-independent pathway). Using ucf-101 we were able to inhibit its protease activity and apoptosis.

UCF-101 was purchased from Nanosyn (Nonoscale Cominatorial Synthesis Inc., 625 Clyde Ave, Mountain View, Calif. 94943-2213

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A method of inhibiting a protein selected from the group consisting of Omi/HtrA2, L56, and bacterial HtrA comprising reacting the protein with a compound of the formula

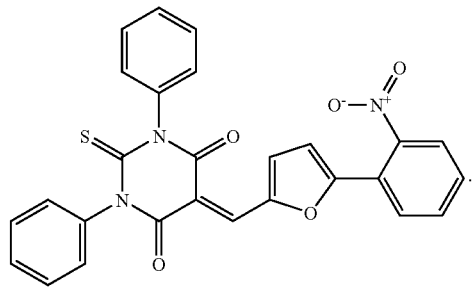

2. A method, as in claim 1, wherein said protein is protein L56.

3. An method, as in claim 1, wherein said protein is bacterial HtrA.

4. A method, as in claim 1, wherein said protein is Omi/HtrA2.

* * * * *

UNITED STATES PATENT AND TRADEMARK OFFICE
CERTIFICATE OF CORRECTION

PATENT NO. : 7,288,546 B1  
APPLICATION NO. : 10/369311  
DATED : October 30, 2007  
INVENTOR(S) : Zervos It is certified that error appears in the above-identified patent and that said Letters Patent is hereby corrected as shown below:

In the Specification

Col. 1, Line 3, insert the following paragraph:

-- This invention was made with government support under DK055734 awarded by the National Institutes of Health. The government has certain rights in the invention. --

Signed and Sealed this  
Seventh Day of January, 2014

Margaret A. Focarino  
*Commissioner for Patents of the United States Patent and Trademark Office*